(12) United States Patent
Aloj et al.

(10) Patent No.: US 12,077,492 B2
(45) Date of Patent: Sep. 3, 2024

(54) METHOD FOR PRODUCING MONOPHASE SALTS OF ACTINIDES AND DEVICE FOR PRODUCING SAME

(71) Applicants: JOINT-STOCK COMPANY «KHLOPIN RADIUM INSTITUTE», St. Petersburg (RU); SCIENCE AND INNOVATIONS—NUCLEAR INDUSTRY SCIENTIFIC DEVELOPMENT, PRIVATE ENTERPRISE, Moscow (RU)

(72) Inventors: Albert Semenovich Aloj, Saint Petersburg (RU); Sergej Evgenevich Samojlov, Leningrad Region (RU); Tatyana Ivanovna Koltsova, g. Saint Petersburg (RU); Mikhail Mikhajlovich Metalidi, Saint Petersburg (RU); Dmitrij Viktorovich Ryabkov, Saint Petersburg (RU); Vasilij Ivanovich Beznosyuk, Gatchina (RU); Vladimir Sergeevich Shchukin, Saint Petersburg (RU); Andrej Yurevich Abashkin, Pos. Murino (RU)

(73) Assignees: JOINT-STOCK COMPANY «KHLOPIN RADIUM INSTITUTE», St. Petersburg (RU); SCIENCE AND INNOVATIONS—NUCLEAR INDUSTRY SCIENTIFIC DEVELOPMENT, PRIVATE ENTERPRISE, Moscow (RU)

( * ) Notice: Subject to any disclaimer, the term of this patent is extended or adjusted under 35 U.S.C. 154(b) by 442 days.

(21) Appl. No.: 17/257,280

(22) PCT Filed: Dec. 5, 2019

(86) PCT No.: PCT/RU2019/050237
§ 371 (c)(1),
(2) Date: Dec. 30, 2020

(87) PCT Pub. No.: WO2020/139168
PCT Pub. Date: Jul. 2, 2020

(65) Prior Publication Data
US 2021/0261490 A1     Aug. 26, 2021

(30) Foreign Application Priority Data
Dec. 25, 2018   (RU) .......................... RU2018146709

(51) Int. Cl.
*C07C 51/41*   (2006.01)
*B01D 1/06*    (2006.01)
(Continued)

(52) U.S. Cl.
CPC .............. *C07C 51/412* (2013.01); *B01D 1/22* (2013.01); *B01D 1/222* (2013.01); *B01D 1/223* (2013.01);
(Continued)

(58) Field of Classification Search
CPC ........ C07C 51/412; B01D 1/225; B01D 1/22; B01D 1/223; B01D 1/222; B01J 19/1887;
(Continued)

(56) References Cited

FOREIGN PATENT DOCUMENTS

DE    2 723 421 A    * 12/1977    ........... C07C 51/412
RU    2 025 059 C1   * 12/1994
(Continued)

OTHER PUBLICATIONS

English translation of RU 2 494 479 C1. (Year: 2013).*
(Continued)

*Primary Examiner* — Daniel Berns
(74) *Attorney, Agent, or Firm* — Jorge Miguel Hernandez; James R. Gourley; Carstens, Allen & Gourley, LLP

(57) ABSTRACT

Method and device for the preparation of monophasic powders of actinide salts which are precursors in the production
(Continued)

of fuel pellets. In one aspect, a compact and simple device is provided to obtain dry monophasic powders of actinide salts in one stage, while increasing the productivity, chemical and nuclear safety of the process. In a second aspect, the method comprises feeding of nitric actinides-containing solution and formic acid to a cylindrical heated reactor, grinding the resulting powder, and discharging the powder. The nitric actinides-containing solution and formic acid are continuously metered to the upper zone of the reactor so that the reactive chemicals are mixed in a thin film on the heat-exchange surface, where the reaction mixture is continuously stirred by rotor blades. Also occurring are the processes of denitration, formation of the relevant compounds, their drying and grinding and collecting dry salts of actinides in a hopper by gravity.

6 Claims, 4 Drawing Sheets

(51) Int. Cl.
*B01D 1/22* (2006.01)
*B01J 19/18* (2006.01)
*G21C 3/62* (2006.01)

(52) U.S. Cl.
CPC .......... *B01D 1/225* (2013.01); *B01J 19/1887* (2013.01); *G21C 3/623* (2013.01)

(58) Field of Classification Search
CPC . B01J 19/18; G21C 3/623; G21C 3/58; C01G 56/00; C01G 56/003; C01G 56/007
See application file for complete search history.

(56) References Cited

FOREIGN PATENT DOCUMENTS

| | | | |
|---|---|---|---|
| RU | 2 494 479 C1 * | 9/2013 | ............. Y02E 30/30 |
| RU | 2 668 920 C1 * | 10/2018 | ............... B01D 1/22 |
| SU | 1 137 313 A * | 1/1985 | |

OTHER PUBLICATIONS

English translation of RU 2 668 920 C1. (Year: 2018).*
English translation of RU 2 025 059 C1. (Year: 1994).*
English translation of SU 1 137 313 A. (Year: 1985).*
English translation of DE 2 723 421 A. (Year: 1977).*

* cited by examiner

METHOD FOR PRODUCING MONOPHASE SALTS OF ACTINIDES AND DEVICE FOR PRODUCING SAME

CROSS-REFERENCE TO RELATED DISCLOSURE

This application is a U.S. National Stage of International Application No. PCT/RU2019/050237 filed on Dec. 5, 2019, and published as WO 2020/139168 on Jul. 2, 2020, titled "Method for Producing Monophase Salts of Actinides and Device for Producing Same," which claims priority to RU 2018146709 filed on Dec. 25, 2018. Each application, publication, and patent listed in this paragraph are hereby incorporated by reference in their entireties.

The invention relates to nuclear engineering, in particular to methods for preparation of monophasic powders of actinide salts which are precursors in the production of fuel pellets.

The methods for the industrial production of monophasic actinide salts powders by co-precipitation of compounds from solutions such as oxalates, polyuranates, or carbonates, are already known. All these methods include filtration operations, filter washing of precipitations, and then their drying in the appropriate atmosphere [Collins, Emory D, Voit, Stewart L, and Vedder, Raymond James. *Evaluation of Co-precipitation Processes for the Synthesis of Mixed-Oxide Fuel Feedstock Materials*, United States: 2011, web. doi: 10.2172/1024695]. A common detriment of precipitation methods is the formation of high volumes of mother and scrubber solutions in the form of RAW which requires disposal.

To eliminate the specified detriments, a method for using direct drying and denitration of actinide nitric acid solution using microwave heating was developed [Teruhiko NUMAO, Hiroshi NAKAYASHIKI, Nobuyuki ARAI, Susumu MIURA, Yoshiharu TAKAHASHI. *Results of Active Test of Uranium—Plutonium Co-denitration Facility at Rokkasho Ryprocessing Plant*, Global 2007, Boise, Idaho, Sep. 9-13, 2007, 238-244].

The method comprises a number of such sequential operations:
1. Scavenging of the mixed solution and its drying at 120° C.
2. Decompounding (denitration) of the molten salts at 150° C.
3. Calcination and distillation of the residual moisture at 250° C. and above
4. Calcination of the mixture and its further oxidation.

The detriments of this method are its multi-stage nature, the need to move the container with the mixture from one furnace to another, and the requirement for additional pulverizing of the resulting sinter.

As a prototype, a method for obtaining actinides solid solutions was chosen [RU2494479, published on Sep. 27, 2013], according to which, a nitric acid solution of actinide nitrates is preheated to 90° C., then formic acid is added in the appropriate proportion, providing a molar ratio of nitrate ion-formic acid (1:3)-(1:4). The reaction mixture is gradually air-dried for 2 hours at 120° C. X-ray fluorescence analysis confirmed the formation of a monophasic mixture of actinide formates (uranyl and plutonium). After calcination of the formate mixture at 400° C. at the output, according to the XRF data, a solid solution of mixed oxides $(U, Pu)O_2$ is obtained.

The detriments of the prototype method include the danger of pre-mixing and hot soaking of nitric acid solutions of actinides with concentrated formic acid. Their interreaction proceeds according to the scheme:

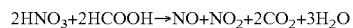
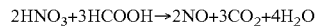

Due to the autocatalytic nature of these reactions, uncontrolled development process with the formation of explosive gas mixtures may occur, so that after mixing of the components, the drying of the reaction mixture should be gradual up to 2 hours, which makes the process periodical and unproductive.

The technical problem to be solved by the claimed invention is to provide a method and device for the preparation of monophasic dry powders of actinide salts that, with a compact and simple device, make it possible to obtain dry powders of actinide salts in a single step while providing improved productivity, chemical and nuclear safety of the process.

To achieve the specified technical result we propose the following: the method of preparation of monophasic powders of actinide salts, which involves feeding of nitric actinides-containing solution and formic acid in the cylindrical heated reactor, grinding the resulting powder, its discharge, characterized in that nitric actinides-containing solution and formic acid are continuously metered to the upper zone of the reactor, thus the reactive chemicals are mixed in a thin film on the heat-exchange surface, where the reaction mixture is continuously stirred by the rotor blades, while sequentially the processes of denitration, formation of the relevant compounds, their drying and grinding and collecting dry salts of actinides in a hopper by gravity.

According to the method, the nitric acid solution containing actinides and formic acid are continuously batched in the molar ratio of the nitrate ion to the formate ion (1:4.3)-(1:4.5), and the temperature of the heat exchange surface is maintained equal to 140±5° C.

The device for preparation of monophasic powders of actinide salts is also proposed in order to achieve this technical result. The proposed device comprises a vertical rotary-film reactor equipped with a heater and chokes for entering the reactive chemicals and removing waste gases, inside which there is a rotor made with the possibility of rotation, with blades fixed along its entire length. The choke for the reactive chemicals input is made in the form of a tee and the intake hopper configured to connect to the reactor vessel to reduce suction of cold air inside it and provided with a heater.

Moreover:
the rotor is welded with four blades, and the gap between the blade edge and the wall is 0.5-1.5 mm;
a tee flow choke for the supply of solutions and a choke for the discharge of the outgoing vapor-gas mixture are located in the upper part of the reactor above the edge of the blades.

Figure 1:
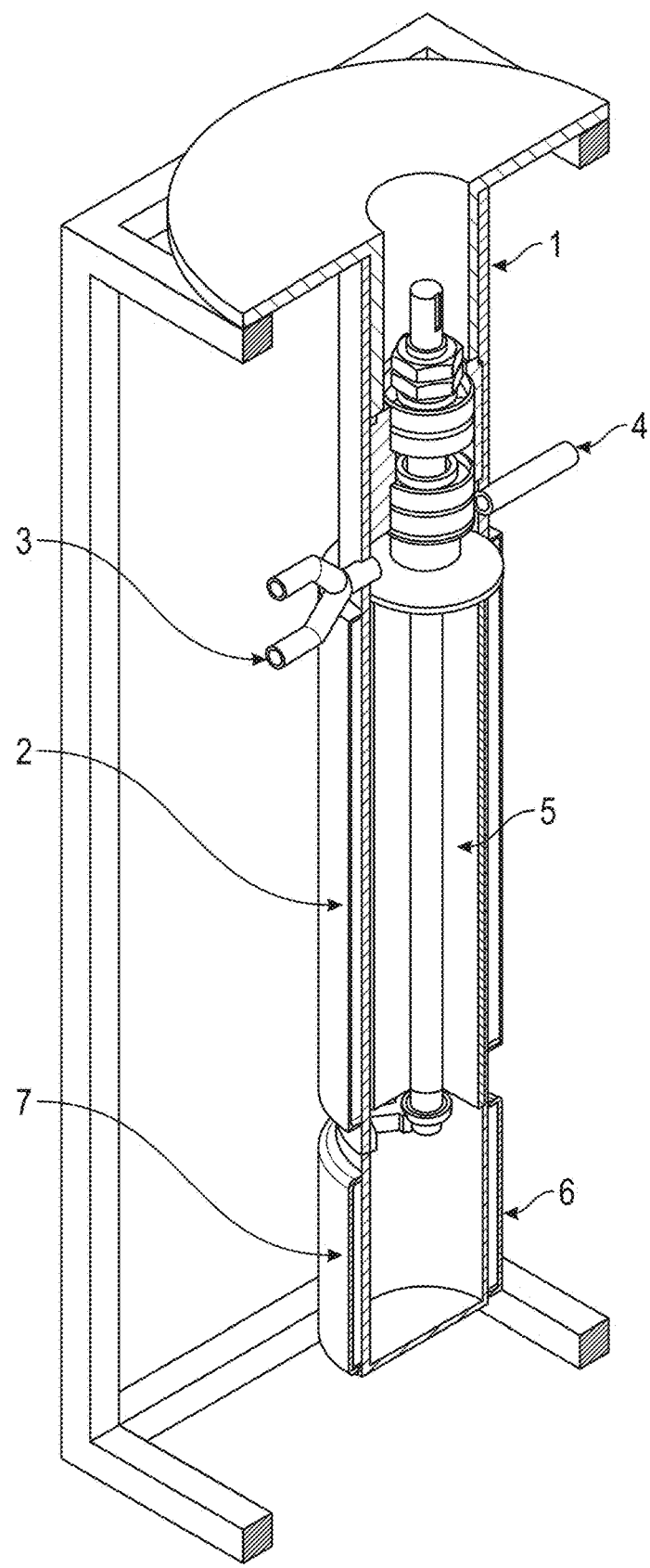
FIG. 1 is the nuclear and explosion-proof device (for implementing a method for producing monophase salts of actinides and device for producing same)

For the purpose of the embodiment of the method, the nuclear and explosion-safe device is used, which is shown in FIG. 1, and which comprises the vertical cylindrical reactor (1), heated by a heater (2), the tee flow choke (3) for separate supply of solutions and the choke (4) for removing the vapor-gas mixture. The reactor (1) comprises a rotor (5) with a distribution disk and blades, the receiving hopper (6) equipped with a heater (7).

The use of the proposed method for obtaining monophasic actinide salts and the proposed device for their preparation provides:
short residence time of reactive chemicals continuously batched under thermal conditions with simultaneous deep evaporation to dry, resulting in increased productivity and safety of the process;
the compactness of the device and the simplicity of its design allows it to be disassembled if necessary for inspection and washing of the internal surfaces;
nuclear safety is ensured by minimizing the amount of nuclear materials in a thin film inside the device when scaling the process and using solutions with a high content of actinides.

The method is as follows:
an actinide-containing nitric acid solution and formic acid are fed separately to the reactor (1) via the choke (3), which is located above the heater (2), to the rotor disk (5) using metering pumps. The reaction mixture is discharged from the rotor disk onto the heated surface of the reactor (1) under the action of centrifugal force when the rotor (5) spins. The rotor blades (5) continuously stir the reaction mixture as it moves from top to bottom along the heat exchange surface, ensuring that dry actinide salts are obtained and collected by gravity in the hopper (6) equipped with a heater (7), and a vapor-gas mixture is removed from the reactor (1) through the choke (4).

Example 1

Figure 2:
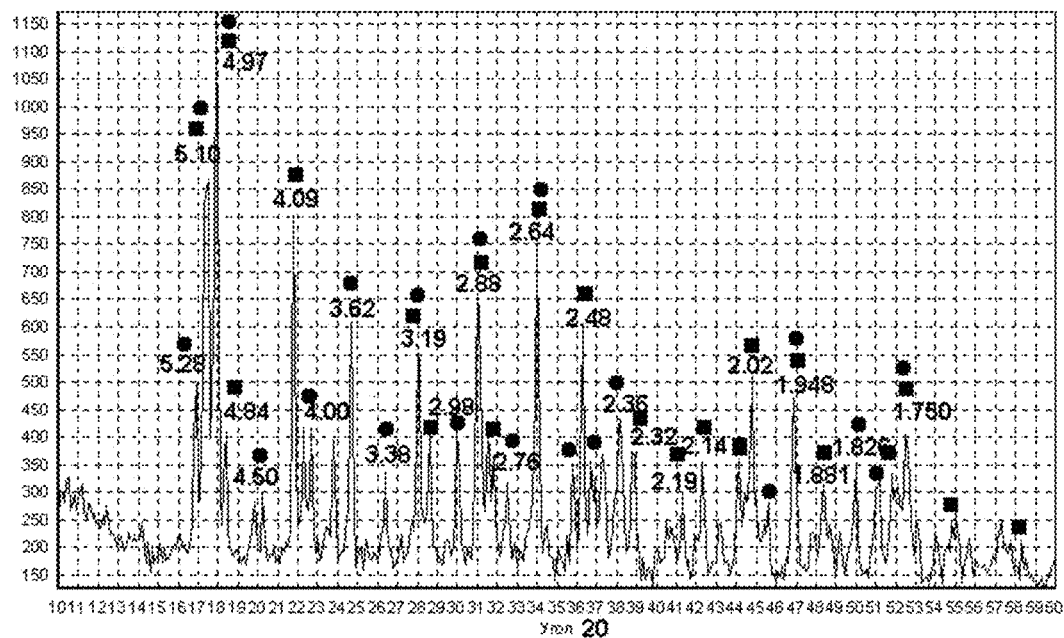
FIG. 2 is the X-ray diffraction pattern of the powder obtained by Example 1, where ● is a compound with the $CH_2O_5U$; structure; ■ is a compound with the $C_2H_2O_6U \cdot H_2O$ structure.

Solutions of uranyl nitrate in 1 molar $HNO_3$ with the uranium concentration of 100 g/l and concentrated formic acid at room temperature are fed separately to the reactor using metering pumps through a tee flow choke, while the molar ratio of nitrate-ion/formic acid is 1:3.6. The temperature on the reactor wall is 142° C., and the temperature on the receiving hopper wall is 145° C. The powder was poured into the receiving hopper homogeneously. According to XRF data, the powder consists of two crystalline phases: 50 wt. % of hydrate formate ($CH_2O_5U$) and 50 wt. % of aqueous formate ($C_2H_2O_6U \cdot H_2O$). The X-ray diffraction pattern of the powder obtained by Example 1 is shown in FIG. 2, where: ● is a compound with the $CH_2O_5U$; structure; ■ is a compound with the $C_2H_2O_6U \cdot H_2O$ structure.

Example 2

Figure 3:
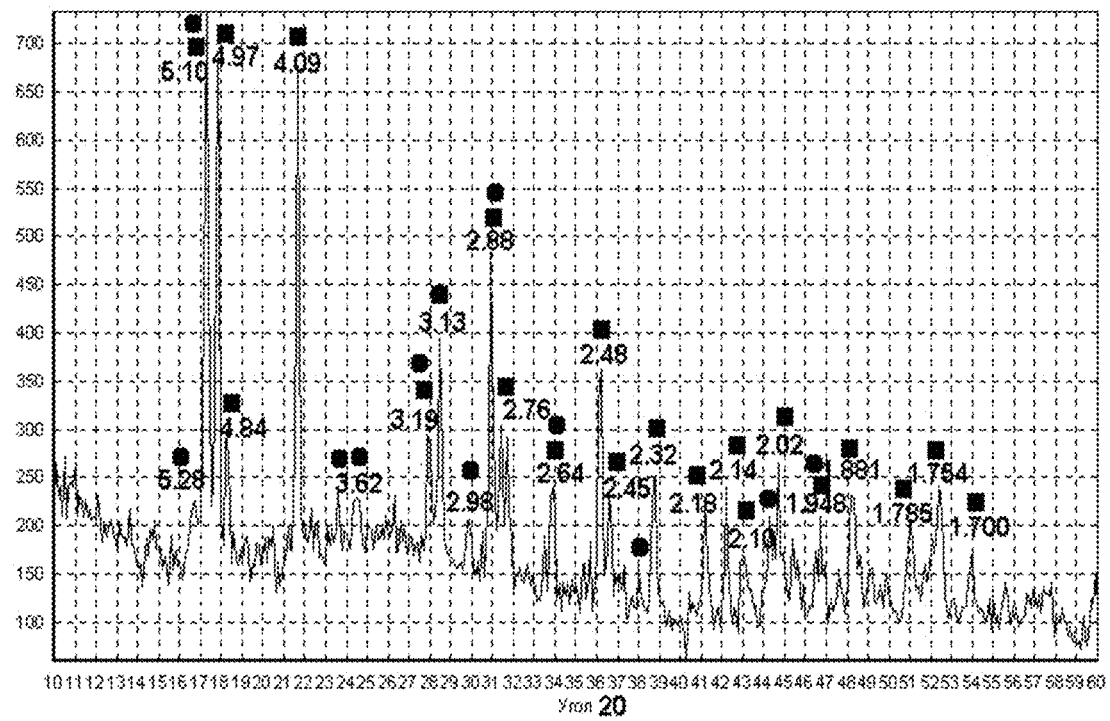
FIG. 3 is the X-ray diffraction pattern of the powder obtained by Example 2, where ● is a compound with the $CH_2O_5U$; structure; ■ is a compound with the $C_2H_2O_6U \cdot H_2O$ structure.

Solutions of uranyl nitrate in 1 molar $HNO_3$ with the uranium concentration of 100 g/l and concentrated formic acid at room temperature are fed separately to the reactor using metering pumps through a tee flow choke, while the molar ratio of nitrate-ion/formic acid is 1:4.0. The temperature on the reactor wall is 140° C., and the temperature on the receiving hopper wall is 130° C. The powder was poured into the receiving hopper homogeneously. According to XRF data, the powder consists of two crystalline phases: 20 wt. % of hydrate formate ($CH_2O_5U$) and 80 wt. % of aqueous formate ($C_2H_2O_6U \cdot H_2O$). The X-ray diffraction pattern of the powder obtained by Example 2 is shown in FIG. 3, where: ● is a compound with the $CH_2O_5U$; structure; ■ is a compound with the $C_2H_2O_6U \cdot H_2O$ structure.

Example 3

Figure 4:
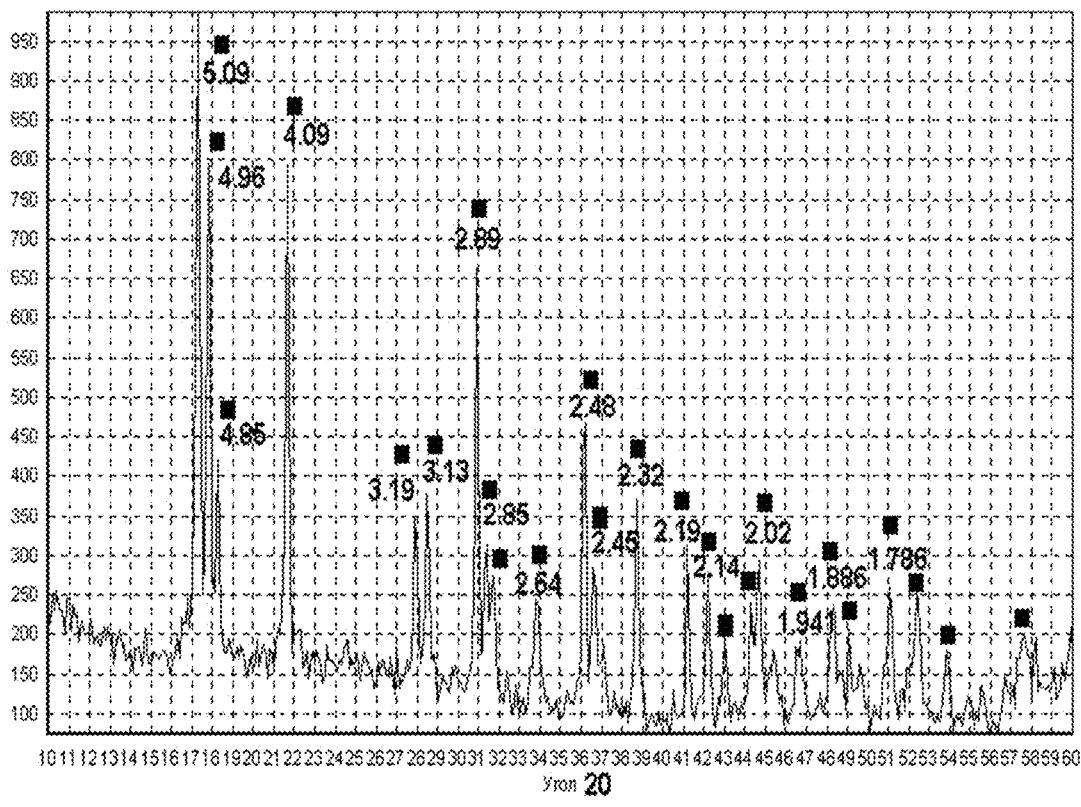
FIG. 4 is the X-ray diffraction pattern of the powder obtained by Example 3, where ■ is a compound with the structure of $C_2H_2O_6U \cdot H_2O$.

Solutions of uranyl nitrate in 1 molar $HNO_3$ with the uranium concentration of 100 g/l and concentrated formic acid at room temperature are fed separately to the reactor using metering pumps through a tee flow choke, while the molar ratio of nitrate-ion/formic acid is 1:4.3. The temperature on the reactor wall is 142° C., and the temperature on the receiving hopper wall is 160° C. The powder was poured into the receiving hopper homogeneously. According to the XRF data, the monophasic powder consists of 100 mass. % of aqueous formate ($C_2H_2O_6U \cdot H_2O$). The X-ray diffraction pattern of the powder obtained by Example 3 is shown in FIG. 4, where: ■ is a compound with the structure of $C_2H_2O_6U \cdot H_2O$.

Example 4

Figure 5:
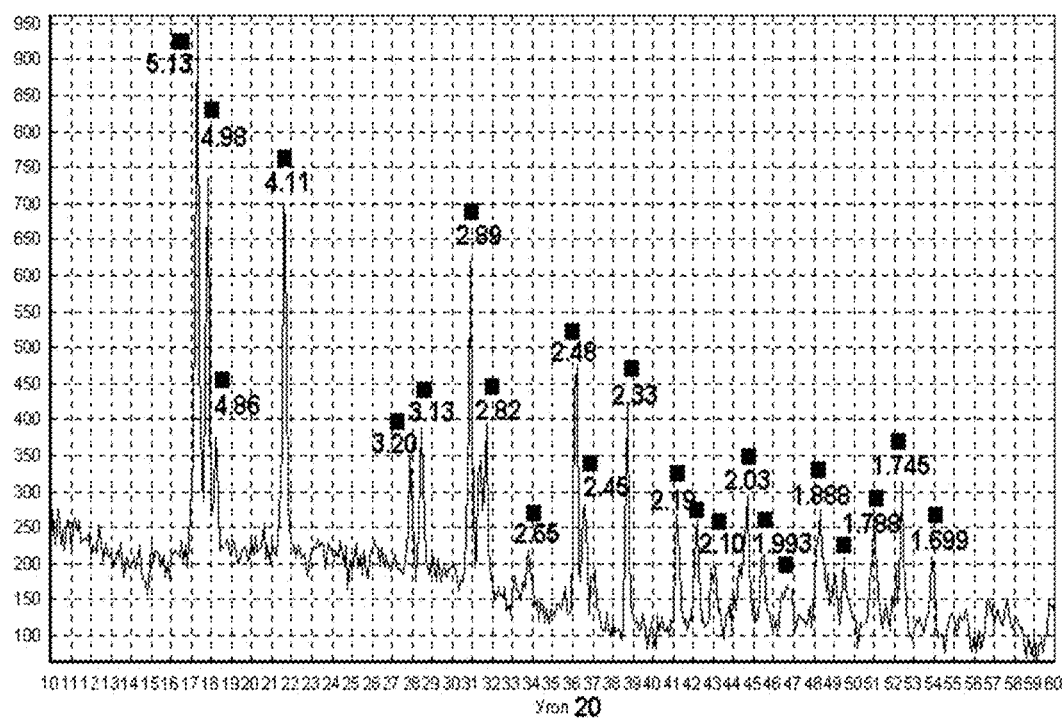
FIG. 5 is the X-ray diffraction pattern of the powder obtained by Example 4, where ■ is a compound with the structure of $C_2H_2O_6U \cdot H_2O$.

Nitric acid solution in 0.845 molar $HNO_3$ with a concentration of 91.1 g/l for uranium, 9.0 g/l for thorium, and concentrated formic acid at room temperature is fed separately to the reactor using metering pumps through a tee flow choke, while the molar ratio of nitrate-ion/formic acid is 1:4.5. The temperature on the reactor wall is 142° C., and the temperature on the receiving hopper wall is 160° C. The powder was poured into the receiving hopper homogeneously, and according to the XRF data comprised a compound with the structure of aqueous formate and the formula of ($C_2H_2O_6(U, Th) \cdot H_2O$). The X-ray diffraction pattern of the powder obtained by Example 4 is shown in FIG. 5, where: ■ is a compound with the structure of $C_2H_2O_6U \cdot H_2O$.

The invention claimed is:

1. A method for producing monophase powders of actinide salts, comprising feeding a solution of one or more nitric actinides and formic acid in a cylindrical heated reactor, thereby forming a powder, grinding the resulting powder, and discharging the grinded powder, characterized in that the solution of one or more nitric actinides and formic acid are continuously metered to the upper zone of the reactor, wherein the solution and formic acid are mixed in a thin film on a heat-exchange surface and continuously stirred by rotor blades, wherein the grinded powder is collected in a hopper by gravity.

2. The method according to claim 1 characterized in that the solution of one or more nitric actinides and formic acid are batched separately and continuously in a (1:4.3)-(1:4.5) molar ratio of nitrate ion and formate ion.

3. The method according to claim 1 characterized in that the heat exchange surface temperature is maintained at 140±5° C.

4. A device for producing monophasic powders of actinide salts, including a vertical rotary-film reactor equipped with a heater, one or more chokers for entering reactive chemicals and for removing a vapor-gas phase, inside which is a rotor, with blades fixed along its entire length, characterized in that the one or more chokers for the reactive chemicals entering is made in the form of a tee, and a receiving hopper is made with the possibility of joining to a reactor and is equipped with a heater.

5. The device according to claim 4 characterized in that the rotor is made welded with four blades, and the gap between the blade edge and the wall is 0.5-1.5 mm.

6. The device according to claim 4 characterized in that the one or more chokers for the supply of solutions and a choke for the discharge of an outgoing vapor-gas phase are located in the upper part of the reactor above the edge of the blades.

\* \* \* \* \*